(12) United States Patent
Almalaq

(10) Patent No.: US 12,075,993 B2
(45) Date of Patent: Sep. 3, 2024

(54) SOLUBLE NEEDLE FOR HAIR TRANSPLANTATION AND MANUFACTURE METHOD THEREOF

(71) Applicant: Sulaiman Abdulmohsin Almalaq, Almadinah (SA)

(72) Inventor: Sulaiman Abdulmohsin Almalaq, Almadinah (SA)

( * ) Notice: Subject to any disclaimer, the term of this patent is extended or adjusted under 35 U.S.C. 154(b) by 22 days.

(21) Appl. No.: 18/107,402

(22) Filed: Feb. 8, 2023

(65) Prior Publication Data

US 2023/0190249 A1 Jun. 22, 2023

Related U.S. Application Data

(63) Continuation of application No. 16/640,712, filed as application No. PCT/CN2018/102109 on May 24, 2018, now Pat. No. 11,642,109.

(51) Int. Cl.
| | | |
|---|---|---|
| *A61B 17/00* | (2006.01) | |
| *A61L 31/04* | (2006.01) | |
| *A61L 31/14* | (2006.01) | |

(52) U.S. Cl.
CPC ............ *A61B 17/00* (2013.01); *A61L 31/042* (2013.01); *A61L 31/048* (2013.01); *A61L 31/148* (2013.01);
(Continued)

(58) Field of Classification Search
CPC .......... A61B 17/00; A61B 2017/00004; A61B 2017/00526; A61B 2017/00752; A61L 31/042; A61L 31/048; A61L 31/148
See application file for complete search history.

(56) References Cited

U.S. PATENT DOCUMENTS

| | | |
|---|---|---|
| 6,379,324 B1 | 4/2002 | Gartstein et al. |
| 6,461,369 B1 | 10/2002 | Kim |
| (Continued) | | |

FOREIGN PATENT DOCUMENTS

| | | |
|---|---|---|
| CN | 1115629 A | 1/1996 |
| CN | 1318992 A | 10/2001 |
| (Continued) | | |

OTHER PUBLICATIONS

State Intellectual Property Offie of the P.R. China; International Search Report and Written Opinion issued in Int'l App. No. PCT/CN2018/102109 dated Nov. 26, 2018; 10 pages.
(Continued)

*Primary Examiner* — Ashley L Fishback
(74) *Attorney, Agent, or Firm* — Maschoff Brennan

(57) ABSTRACT

A soluble needle (100) for hair transplantation, wherein the soluble needle (100) comprises a fixing plate (30) and a plurality of micro-needles (20) made of water-soluble polymers arranged on the fixing plate (30), wherein each of said micro-needle (20) comprises a needle wall (21) to penetrate scalps and a needle cavity (22) confined by the needle wall (21) and configured for accommodating a hair follicle. A method of manufacturing a soluble needle (100) for hair transplantation, wherein the method includes: dissolving water-soluble polymers in water to prepare a molding solution (S101); delivering the molding solution into a mold (S102); letting the molding solution settle in the mold to shape (S103); and separating and removing the mold to produce the soluble needle (S104). The soluble needle (100) effectively shortens the time of surgery, reduces the pain of the patients, and increases the viability rate of transplanted hair follicles.

20 Claims, 4 Drawing Sheets

(52) U.S. Cl.
CPC ........... *A61B 2017/00004* (2013.01); *A61B 2017/00526* (2013.01); *A61B 2017/00752* (2013.01); *A61B 2017/00876* (2013.01); *A61B 2017/00942* (2013.01)

(56) References Cited

U.S. PATENT DOCUMENTS

| | | |
|---|---|---|
| 2002/0045907 A1 | 4/2002 | Sherman et al. |
| 2007/0078376 A1 | 4/2007 | Smith |
| 2007/0149985 A1 | 6/2007 | Cole |
| 2011/0172609 A1 | 7/2011 | Moga et al. |
| 2011/0313429 A1 | 12/2011 | Anderson et al. |
| 2016/0015416 A1 | 1/2016 | Franco et al. |
| 2016/0166819 A1 | 6/2016 | Simmers |
| 2017/0189660 A1 | 7/2017 | Baek |

FOREIGN PATENT DOCUMENTS

| | | |
|---|---|---|
| CN | 103893018 A | 7/2014 |
| CN | 105031744 A | 11/2015 |
| CN | 105496474 A | 4/2016 |
| CN | 106902453 A | 6/2017 |
| CN | 107334495 A | 11/2017 |
| CN | 107334496 A | 11/2017 |
| KR | 20160128888 A | 11/2016 |
| KR | 20160142691 A | 12/2016 |
| KR | 1017285260000 | 4/2017 |
| WO | 2016033540 A1 | 3/2016 |

OTHER PUBLICATIONS

European Search Report issued in corresponding application No. 18848747.4, dated Mar. 24, 2021.

```
┌─────────────────────────────────────┐
│ Dissolving the water-soluble polymers │──── S101
│ in water to prepare a molding solution│
└─────────────────────────────────────┘
                 │
                 ▼
┌─────────────────────────────────────┐
│ Delivering the molding solution into a mold │──── S102
└─────────────────────────────────────┘
                 │
                 ▼
┌─────────────────────────────────────┐
│ Letting the molding solution settle  │──── S103
│        in the mold to shape          │
└─────────────────────────────────────┘
                 │
                 ▼
┌─────────────────────────────────────┐
│ Separating and removing the mold to  │──── S104
│     produce the soluble needle       │
└─────────────────────────────────────┘
```

Fig. 6

```
┌────────────────────────────────────────────────┐
│ Letting the molding solution settle statically in the │──── S1031
│  mold at an ambient temperature of 25 ° C to 70       │
│  ° C, and with a settling time between 3 h and 24 h   │
└────────────────────────────────────────────────┘
```

Fig. 7

```
┌─────────────────────────────────────┐
│   Performing degassing treatment     │──── S201
│       to the molding solution        │
└─────────────────────────────────────┘
```

Fig. 8

```
┌────────────────────────────────────────────────────────┐
│ Injecting the molding solution into the mold, wherein the │──── S1021
│ mold includes a plurality of mold cavities corresponding to│
│ the plurality of micro-needles, and the volume of molding  │
│ solution injected into each mold cavity is less than the   │
│ capacity of the mold cavity, so as to form a needle cavity in│
│ the to-be-molded micro-needle structure in each mold cavity│
└────────────────────────────────────────────────────────┘
```

Fig. 9

```
┌────────────────────────────────────────────────────────┐
│ Creating a through hole for each to-be-molded micro-needle │
│  structure in each mold cavity, so as to form a pinhole at the│──── S1032
│ tip of the each to-be-molded micro-needle structure, with the │
│     pinhole communicating with the needle cavity          │
└────────────────────────────────────────────────────────┘
```

Fig. 10

SOLUBLE NEEDLE FOR HAIR TRANSPLANTATION AND MANUFACTURE METHOD THEREOF

CROSS-REFERENCE TO RELATED APPLICATIONS

The present application is a continuation of U.S. application Ser. No. 16/640,712 filed Feb. 20, 2020, which is a section 371 nationalization of PCT Application No. PCT/CN2018/102109 filed Aug. 24, 2018, which claims priority to Chinese Patent Application No. 201710733590.2 filed Aug. 24, 2017, wherein the entire contents of these applications are incorporated herein by reference.

FIELD OF THE INVENTION

The present disclosure relates to the technical field of hair transplantation devices, in particular to a soluble needle for hair transplantation and a method of manufacturing the same.

BACKGROUND

Many people suffer from hair loss due to age, genetics, and other factors, and now this problem could be solved by hair transplantation technologies. The common method of hair transplantation comprises extracting hair follicles from the back of the head of a human as sources of hairs, with the hair sources separated as single or multiple hair follicular units, directly transplanting the separated hair follicular units to the receiving sites on human bodies (e.g. scalps, eyebrow, lower jaws, chests, eyelids, pubic areas etc.) by precise microsurgeries, to make the transplanted hair follicular units survive at the new sites and naturally grow, so as to modify and increase the distribution and density of the hairs at local areas.

In the prior hair transplantation microsurgeries, small holes are usually created firstly by puncturing the scalp with 18 G or 19 G needles, and subsequently hair follicles are picked up from the root and delivered into the resulted holes by small tweezers. Since usually a large number of hair follicles are required for the hair transplantation surgery, the hair transplantation surgery process is tedious and time-consuming, and the repeated process of scalp puncturing introduces great pain to the patient. Furthermore, the micro-surgery requires precise operations under microscope for a long time, and misoperations could easily cause damage to the hair follicles, resulting in hair follicles failing to grow well, affecting the viability rate of transplanted hair follicles.

SUMMARY OF THE INVENTION

In view of this, the present disclosure aims to provide a soluble needle for hair transplantation and a method of making the same, wherein the use of the soluble needle for hair transplantation of the present disclosure can provide a higher viability rate of transplanted hair follicles, a better hair transplantation effect, a more convenient hair transplantation process, and a shorter surgery time.

One aspect of the embodiments of the present disclosure provides a soluble needle for hair transplantation, comprising: a fixing plate and a plurality of micro-needles made of water-soluble polymers and arranged on the fixing plate, said micro-needles each comprising a needle wall to penetrate a scalp, and a needle cavity confined by the needle wall and configured for accommodating a hair follicle.

Optionally, said micro-needle is made of hyaluronic acid or polyvinyl alcohol.

Optionally, the needle walls of said plurality of micro-needles are connected to each other; or, the needle walls of said plurality of micro-needles are connected to each other through a connecting layer, and the connecting layer is made of the same material as the micro-needles.

Optionally, said plurality of micro-needles are evenly arranged on the fixing plate.

Optionally, said plurality of micro-needles are arranged at a density of 20 to 40 needles/cm$^2$ on the fixing plate.

Optionally, said plurality of micro-needles are tapered in structure.

Optionally, the tip of the micro-needle is provided with a pinhole running through the needle wall and communicating with the needle cavity.

Optionally, the micro-needle is in a conical structure, the apex angle of the micro-needle is between 15° and 20°, and the diameter of the bottom surface of the micro-needle is between 2.2 mm and 2.8 mm.

Optionally, the thickness of the needle wall is between 0.8 mm and 1.2 mm.

Optionally, said fixing plate is a fixing film layer, and the fixing film layer is configured to be attached by the micro-needles.

Optionally, said plurality of micro-needles are each fixedly connected to said fixing plate through one side of the needle cavity, and the fixing plate is made of the same material as the micro-needles.

Optionally, the fixing plate and the micro-needles are detachably connected to each other.

Another aspect of the embodiments of the present disclosure provides a method for manufacturing a soluble needle for hair transplantation, comprising:
dissolving the water-soluble polymers in water to prepare a molding solution;
delivering the molding solution into a mold;
letting the molding solution settle in the mold to shape; and
separating and removing the mold to produce the soluble needle.

Optionally, the mass fraction of the molding solution is 15 to 25 wt %.

Optionally, said letting the molding solution settle in the mold to shape includes letting the molding solution settle statically in the mold at an ambient temperature of 25° C. to 70° C., for a settling time of 3 h-24 h.

Optionally, said method includes performing degassing treatment on the molding solution before letting the molding solution settle in the mold to shape.

Optionally, delivering the molding solution into a mold includes injecting the molding solution into the mold, wherein the mold includes a plurality of mold cavities corresponding to said plurality of micro-needles, and the volume of molding solution injected into each mold cavity is less than the capacity of the mold cavity, so as to form a needle cavity in the to-be-molded micro-needle structure in each mold cavity.

Optionally, said letting the molding solution settle in the mold to shape includes creating a through hole for each to-be-molded micro-needle structure in each mold cavity, so as to form a pinhole at the tip of the each to-be-molded micro-needle structure, with the pinhole communicating with the needle cavity.

Embodiments of the present disclosure provide a soluble needle for hair transplantation and a method of making the same, the soluble needle comprising a fixing plate and a plurality of micro-needles made of water-soluble polymers and arranged on the fixing plate, said micro-needles each comprising a needle wall to penetrate the scalp and a needle cavity confined by the needle wall and configured for accommodating a hair follicle. When applying the soluble needles in the embodiments of the present disclosure in the hair transplantation surgery, the hair follicles to be transplanted are transferred into the needle cavities of the micro-needles in advance, and during the surgery the micro-needle portions of the soluble needles for hair transplantation are inserted into the dermis of the scalp and remain in the sites of the scalp. As the water-soluble polymers of the micro-needles are gradually dissolved in blood or sweat and absorbed by the human body, the hair follicles accommodated in the needle cavities come into contact with the blood in the dermis and become viable and start to grow. This process effectively shortens the time of surgery, reduces the pain of the patients, and increases the viability rate of transplanted hair follicles.

For better understanding of the purposes, features, and advantages of the present disclosure, exemplary embodiments will be described in greater details in accordance with the accompanying drawings in the following.

BRIEF DESCRIPTION OF THE FIGURES

For clearer description of the technical solutions of the embodiments of the present disclosure, the drawings accompanying the embodiments will be briefly described below. It should be understood that the following drawings demonstrate only exemplary embodiments of the present disclosure, and should not be considered as limitations on the scope of the present disclosure, for those skilled in the art other related drawings can be obtained based on the given drawings without any creative work.

FIG. 6 demonstrates a first flow chart of a method of manufacturing a soluble needle in an embodiment of the present disclosure;

FIG. 7 demonstrates a second flow chart of a method of manufacturing a soluble needle in an embodiment of the present disclosure;

FIG. 8 demonstrates a third flow chart of a method of manufacturing a soluble needle in an embodiment of the present disclosure;

FIG. 9 demonstrates a fourth flow chart of a method of manufacturing a soluble needle in an embodiment of the present disclosure;

FIG. 10 demonstrates a fifth flow chart of a method of manufacturing a soluble needle in an embodiment of the present disclosure;

Figure 1:
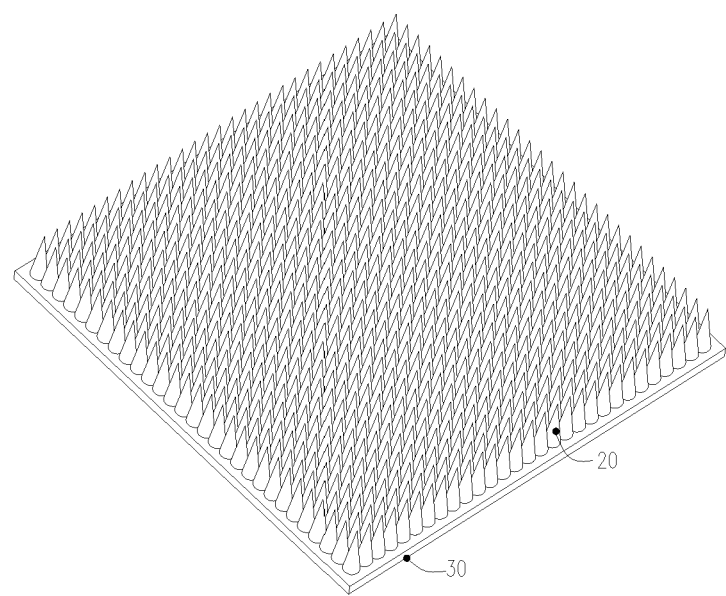
FIG. 1 demonstrates a schematic three-dimensional structure view of a soluble needle in an embodiment of the present disclosure.

Reference numbers. 100—soluble needle; 20—micro-needle; 21—needle wall; 22—needle cavity; 23—connecting layer; 24—pinhole; 30—fixing plate.

DETAILED DESCRIPTION OF THE INVENTION

For better illustration of the purposes, technical solutions, and advantages of the present disclosure, the technical solutions in the embodiments of the present disclosure will hereinafter be clearly and comprehensively described in combination with the drawings of the embodiments of the present disclosure. Obviously, the embodiments described herein are only preferred embodiments and are not all possible embodiments of the present disclosure. The components of the disclosed embodiments, which are described and illustrated in the drawings herein, may generally be arranged and designed in various alternative configurations.

Therefore, the detailed description of the embodiments of the present disclosure herein, should not be considered as limitations on the scope of the present disclosure, but merely examples of selected embodiments of the present disclosure. Any other embodiments which those skilled in the art can obtain without any creative work based on the embodiments of the present disclosure herein should all fall within the scope of the present disclosure.

It should be noted that similar symbols and letters represent similar elements in the drawings hereinafter. Therefore, once an element is defined in one drawing, no further definition or explanation is needed for the same element in subsequent drawings. In the descriptions of the present disclosure, it should be understood that, the terms "longitudinal", "transversal", "on", "under", "in front of", "behind", "left", "right", "vertical", "horizontal", "top", "bottom", "inside", "outside", etc. that indicate the directions or positions based on the directions or positions shown in the drawings or the directions or positions in which the inventive product is commonly placed, are only for the purpose of describing the present disclosure and simplifying the descriptions, but not intended to indicate or imply that a device or a component has a compulsory position or must be structured or operated in a specific position, hence not to be considered as limitations to the present disclosure.

In this description, the illustrative expressions with the above terms are not necessarily referring to the same embodiments or examples. In addition, specific features, structures, materials, or characteristics described may be combined in appropriate manners in any one or more embodiments or examples.

In addition, terms "first", "second", etc. are for description purposes only and should not be considered to be indicating or implying importance in relativity or implicitly indicating the number of the technical features referred to. Therefore, features determined by "first", "second", etc. may explicitly or implicitly contain one or more of the same features. In the description of present disclosure, "a plurality of" means two or more, unless otherwise specified.

In the description of present disclosure, it should be noted that terms "arrange", "attach", "connect" should be perceived with generalized meanings, for instance, "connect" could mean to mechanically connect or electrically connect, to connect internally between two components, to connect directly, or to connect through media. Those skilled in the art should be able to perceive the specific meanings of the above terms base on specific context.

The present disclosure will be further described in detail according to the specific embodiments in combination with drawings.

Figure 3:
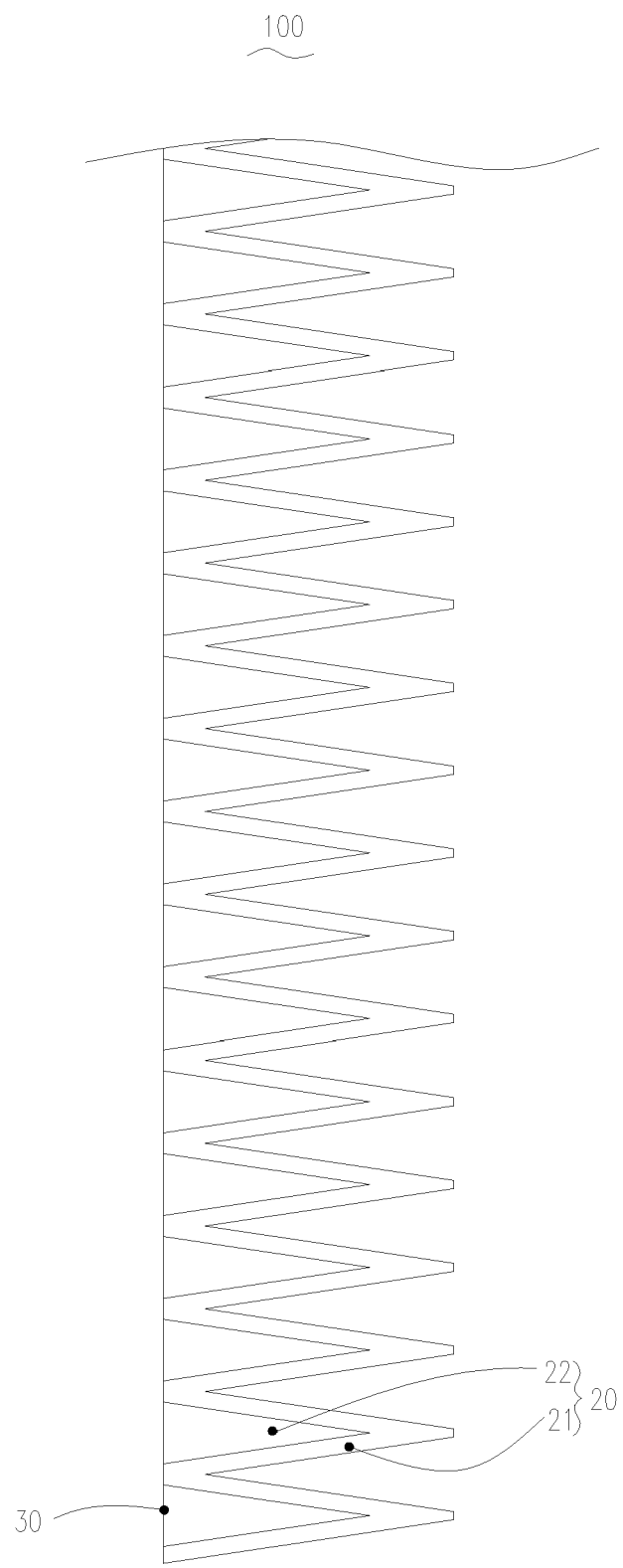
FIG. 3 demonstrates a cross-sectional view taken along line A-A of FIG. 2.

An embodiment of the present disclosure provides a soluble needle 100 for hair transplantation, as shown in FIG. 1, comprising: a fixing plate 30, and a plurality of micro-needles 20 made of water-soluble polymers and arranged on the fixing plate 30, said micro-needles 20 each comprising a needle wall 21 to penetrate the scalp and a needle cavity 22 confined by the needle wall 21 and configured for accommodating the hair follicle, as shown in FIG. 3.

It should be noted that firstly, when manufacturing the soluble needle 100 for hair transplantation in this embodiment of the present disclosure, the hair follicles to be transplanted are transferred into the needle cavities 22 of the micro-needles 20 in advance, so that in the surgery using the soluble needles 100 for hair transplantation, the soluble needles 100 are attached to the scalp on the side where micro-needles 20 are configured, and the needle portions of the micro-needles 20 penetrate deeply into the dermis of the scalp. As the water-soluble polymers of the micro-needles 20 start to dissolve gradually in blood or sweat and to be absorbed gradually by the human body, the hair follicles accommodated in the needle cavities 22 come into contact with the blood in the dermis and become viable and grow, during which process no human intervention or other operations are necessary, providing a stable environment for the hair follicles to survive and grow at the new sites.

Secondly, this embodiment of the present disclosure does not set limitations to the shape and material of the fixing plate. Generally, the micro-needles 20 are arranged on the fixing plate 30 in a dense manner so as to improve the efficiency of the surgery. Illustratively, as shown in FIG. 1, the fixing plate 30 is of rectangular shape. As one example, when the fixing plate 30 is made of the same water-soluble polymer as the micro-needles 20, the fixing plate 30 can dissolve gradually as the micro-needles 20 dissolve and can then be wiped away by soft tissues or clothes, after the soluble needles 100 are attached to the scalp and the micro-needles 20 penetrate deeply into the dermis of the scalp. As another example, when the fixing plate 30 is made of other non-soluble material, the fixing plate 30 can be removed after the micro-needles 20 are dissolved and absorbed by human body and the hair follicles become viable and start to grow in the dermis of the scalp.

Thirdly, a water-soluble polymer is also called a water-soluble resin. It is a highly hydrophilic polymeric material that dissolves or swells in water to form an aqueous solution or dispersion system. There is a large amount of hydrophilic groups in the molecular structure of the water-soluble polymer. There may be three types of hydrophilic groups: 1 cationic groups, such as tertiary amine group, quaternary amine group, etc.; 2 anionic groups, such as carboxylic acid group, sulfonic acid group, phosphoric acid group, sulfuric acid group, etc.; 3 polar nonionic groups, such as hydroxyl group, ether group, amine group, amide group, etc. The water-soluble polymer materials for manufacturing the micro-needles 20 in the embodiment of the present disclosure may be natural water-soluble polymers from natural animals and plants sources, such as starch, cellulose, vegetable gums, animal gels, etc.; chemically modified natural polymers, such as carboxymethyl starch, starch acetate, hydroxymethyl cellulose, carboxymethyl cellulose, etc.; or synthetic polymers (including polymerization resin and condensation resin), such as polyacrylamide (PAM), hydrolyzed polyacrylamide (HPAM), polyvinyl pyrrolidone (PVP). The water-soluble polymers may also be divided into non-ionic polymers and ionic polymers based on the hydration groups on the macromolecular chains. The water-soluble polymers may also be divided into nonionic polymers, cationic polymers, anionic polymers, and zwitterionic polymers (latter three being polyelectrolytes) based on electric charges. The water-soluble polymers may also be divided into associated polymers and non-associated polymers based on whether there are strong non-covalent bonds between the groups. This embodiment of the present disclosure does not set limitations to the above-mentioned types of the water-soluble polymer. Any water-soluble polymer that can dissolve and be absorbed when puncture into human skin falls within the scope.

Fourthly, this embodiment of the present disclosure does not set limitations to the shape of the micro-needles 20. The micro-needles 20 only need to be able to penetrate the scalp with the needle walls 21 and enter the dermis of the scalp so that the hair follicles accommodated in the needle cavities 22 can come into contact with the dermis and become viable and grow. Accordingly, this embodiment of the present disclosure does not set limitations to the shape and size of the needle cavities 22. Since the purpose of the needle cavities 22 is to accommodate the hair follicles, the needle cavities 22 only need to be able to accommodate hair follicles and be able to expose the hair follicles to the dermis when the micro-needles 20 dissolve so that the hair follicles could become viable and start to grow.

The embodiment of the present disclosure provides a soluble needle 100 for hair transplantation, comprising: a fixing plate 30 and a plurality of micro-needles 20 made of water-soluble polymers arranged on the fixing plate 30, said micro-needles 20 each comprising a needle wall 21 to penetrate the scalp and a needle cavity 22 confined by the needle wall 21 and configured for accommodating the hair follicles. When applying the soluble needle 100 in this embodiment of the present disclosure in the hair transplantation surgery, the hair follicles to be transplanted are transferred into the needle cavities 22 of the micro-needles 20 in advance. During the surgery the micro-needles 20 of the soluble needle 100 are aimed at the scalp and the micro-needles 20 penetrate the scalp and enter the dermis of the scalp with the remaining of the soluble needle 100 left on the scalp. As the water-soluble polymers of the micro-needles 20 dissolve in blood or sweat and to be absorbed by the human body gradually, the hair follicles accommodated in the needle cavities 22 come into contact with the blood in the dermis and become viable and start to grow. This process effectively shortens the time of surgery, reduces the pain of the patients, and increases the viability rate of transplanted hair follicles.

Optionally, the micro-needles 20 are made of hyaluronic acid or polyvinyl alcohol.

The water-soluble polymer may include any one of hyaluronic acid or polyvinyl alcohol, and may also include other biodegradable polymers. Hyaluronic acid is a higher polysaccharide consisting of units of D-glucuronic acid and N-acetylglucosamine. D-glucuronic acid and N-acetylglucosamine are linked by a β-1,3-glycosidic bonds, and the disaccharide units are linked by a β-1,4-glycosidic bonds. Number of the disaccharide units can be up to 25000 The molecular weight of hyaluronic acid in human body ranges from 5,000 to 20,000,000 Dalton, with a general molecular formula $(C_{14}H_{21}NO_{11})n$.

As one example, in this embodiment of the present disclosure, the micro-needles 20 are made of hyaluronic acid. Hyaluronic acid can improve skin growth conditions. Specifically, hyaluronic acid can form a breathable film on the skin surface to make the skin smooth and moist, and prevent the invasion of foreign bacteria, dust, and ultraviolet light, hence to protect the skin from damages. Hyaluronic acid can also infiltrate into the dermis, providing functions of slight expansion of capillaries, blood circulation improvement, intermediate metabolism improvement, and accelerated skin nutrient absorption, and has a strong wrinkle-reducing effect, which can increase elasticity of skin and delay ageing. Hyaluronic acid can further promote the proliferation and differentiation of epidermal cells, get rid of free oxygen radicals, and prevent and repair skin damage. The aqueous solution of hyaluronic acid is highly viscous, which can thicken aqueous phase or stabilize the emulsion, which achieves uniform and fine paste after emulsified with oil phase.

As another example, the micro-needles 20 can also be made of polyvinyl alcohol (PVA). PVA has a general molecular formula of

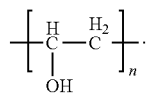

In this embodiment of the present disclosure, PVA is preferably selected to be medical grade PVA, e.g. EG-05P, EG-05, EG-40, etc. Specifically, PVA may be PVA 0588 or PVA 1788.

Figure 2:
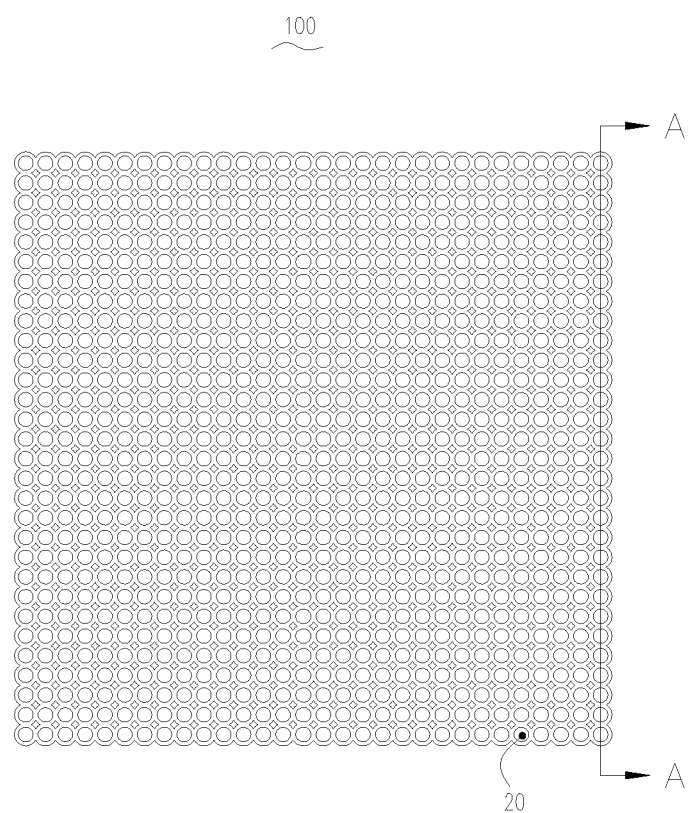
FIG. 2 demonstrates a first schematic view showing a plurality of micro-needles in an embodiment of the present disclosure.
Figure 4:
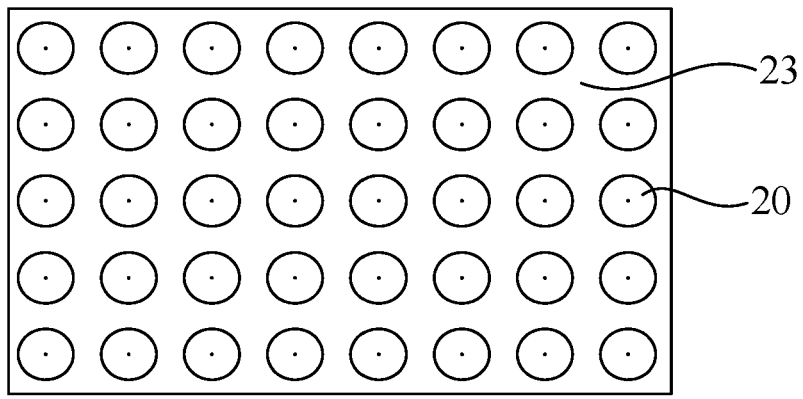
FIG. 4 demonstrates a second schematic view showing a plurality of micro-needles in an embodiment of the present disclosure.

Optionally, as shown in FIG. 2, the needle walls 21 of a plurality of the micro-needles 20 are connected to each other; or, as shown in FIG. 4, the needle walls 21 of a plurality of the micro-needles 20 are connected to each other through a connecting layer 23, and the connecting layer 23 is made of the same material as the micro-needles 20.

As one example, shown in FIG. 2, the needle walls 21 of a plurality of the micro-needles 20 are connected to each other, so that a plurality of the micro-needles 20 form a unity and may connect with the fixing plate 30. As a result, when the micro-needles 20 are arranged on the fixing plate 30, a plurality of micro-needles 20 connected to each other can be arranged onto the fixing plate 30 as a unity, rather than to tediously arrange individual micro-needles 20 one by one, and therefore could improve the speed and efficiency of arrangement for the plurality of micro-needles 20 onto the fixing plate 30.

As another example, as shown in FIG. 4, when the micro-needles 20 are arranged on the fixing plate 30 (not shown in FIG. 4, see FIG. 1) in a less dense manner, the needle walls 21 of every two neighboring micro-needles 20 are connected by a connecting layer 23, wherein the connecting layer 23 is made of the same material as the micro-needles 20. As a result, as the micro-needles 20 dissolve in blood or sweat and to be absorbed gradually after penetrate the scalp and enter the dermis of the scalp, the connecting layer 23 also dissolves gradually, and the dissolved connecting layer 23 could be wiped away by soft tissues or clothes, so that, when manufacturing the soluble needle 100 in this embodiment of the present disclosure, a plurality of micro-needles 20 connected by the connecting layer 23 could be arranged as a unity, improving the speed and efficiency of arrangement for the plurality of micro-needles 20 onto the fixing plate 30, and that, after the hair transplantation surgery using the soluble needle 100 in this embodiment of the present disclosure, a step of removing the connecting layer 23 is not needed.

Optionally, as shown in FIG. 1, a plurality of micro-needles 20 are evenly arranged on the fixing plate 30.

Illustratively, the micro-needles 20 are evenly arranged on the fixing plate 30, wherein the specific manner of arrangement is transversal and longitudinal. Herein transversal and longitudinal arrangement means arrangement as a matrix with rows and columns. As an example, micro-needles 20 can be arranged in 30 rows and 30 columns. When the hair follicles accommodated in the evenly arranged micro-needles 20 are transplanted to and grow in the scalp, they will have an even and natural distribution.

Optionally, a plurality of micro-needles 20 are arranged at a density of 20 to 40 needles/cm$^2$ on the fixing plate 30.

Since the hair follicles in the human scalp grow following certain natural laws, too high a density of the transplanted hair follicles would result in a low viability rate of the hair follicles, and too low a density of the transplanted hair follicles would affect the visual effect of the transplanted hairs. Therefore, micro-needles 20 are arranged at a density of 20 to 40 needles/cm$^2$ on the fixing plate 30. As an example, the number of micro-needles 20 arranged evenly on every square centimeter of the fixing plate 30 is between 20 and 40, e.g. 20, 22, 25, 30, 35, 38, 40, etc.

The micro-needles 20 are configured in tapered structure, so that firstly it facilitates the needle cavities to form as the bottom of the tapered structure, and secondly the sharp tips of the tapered structure facilitate the micro-needles 20 to penetrate the scalp and enter the dermis in the hair transplantation surgery.

Optionally, as shown in FIG. 1, the micro-needles 20 are tapered in structure.

The micro-needles 20 are configured in tapered structure, so that firstly it facilitates the formation of the needle cavities in the bottom of the tapered structure, and secondly the sharp tips of the tapered structure facilitate the micro-needles 20 to penetrate the scalp and enter the dermis in the hair transplantation surgery.

Figure 5:
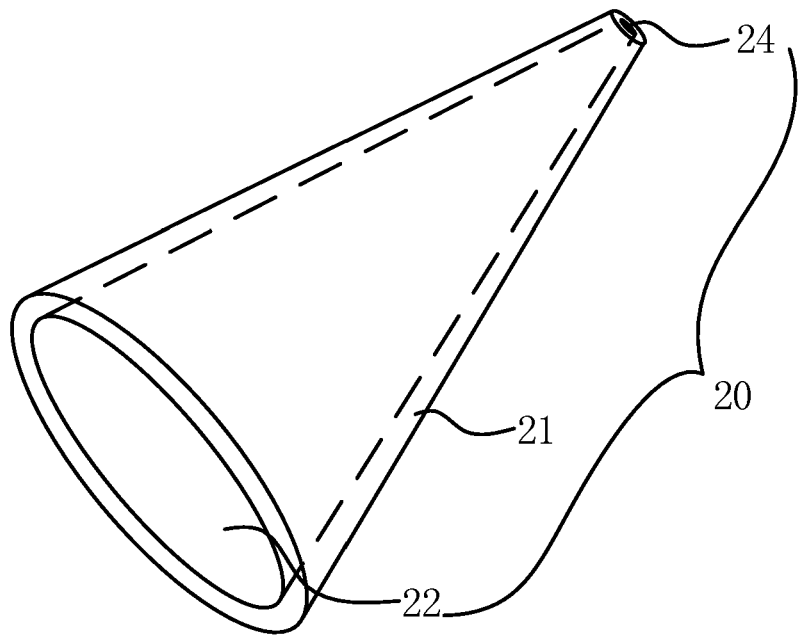
FIG. 5 demonstrates a schematic structural diagram of a single micro-needle in an embodiment of the present disclosure.

Optionally, as shown in FIG. 5, the tip of the micro-needle 20 is provided with a pinhole 24 running through the needle wall 21 and communicating with the needle cavity 22.

As a result, when the soluble needle 100 in this embodiment of the present disclosure is applied in hair transplantation surgery and the micro-needles 20 penetrate the scalp and enter the dermis of the scalp, due to the pinhole 24 provided on the tip being communicating with the needle cavity 22, the hair follicles accommodated in the needle cavities 22 are able to be exposed to the blood and start to grow even before the micro-needles 20 start to dissolve, so that the hair follicles will have earlier contact with the human body and therefore the viability rate of the transplanted hair follicles will be improved.

Optionally, as shown in FIG. 1, the micro-needles 20 have a conical structure, the apex angle of the micro-needle 20 is between 150 and 20°, and the diameter of the bottom surface of the micro-needle 20 is between 2.2 mm and 2.8 mm.

Illustratively, in the embodiment wherein the micro-needles 20 are of conical structure, the apex angle of the micro-needle 20 can be configured between 15° and 20°, e.g. 15°, 16°, 17.06°, 19°, 19.5°, 20°, etc. When the apex angle is larger than 20°, the conical structure may have too large an apex angle, resulting in a relatively large bottom surface area of the micro-needle 20 if keeping other parameters unchanged, and therefore causing difficulties in arranging the micro-needles 20 at a relatively high density on the fixing plate 30. When the apex angle is smaller than 15°, the volume of the needle cavity 22 of the micro-needle 20 may be too small to accommodate the hair follicle. Moreover, the diameter of the bottom surface of the micro-needle 20 is configured between 2.2 mm and 2.8 mm, e.g. 2.2 mm, 2.25 mm, 2.3 mm, 2.4 mm, 2.5 mm, 2.8 mm, etc. As a result, provided that there is sufficiently large volume of the needle cavity 22, individual micro-needles 20 is prevented from occupying too large area on the fixing plate 30 and leading to insufficiently dense arrangement of micro-needles 20 on the fixing plate 30.

Optionally, the thickness of the needle wall 21 is between 0.8 mm and 1.2 mm, e.g. 0.8 mm, 0.85 mm, 0.9 mm, 1 mm, 1.1 mm, 1.2 mm, etc. As a result, provided that the needle wall 21 is stiff enough to penetrate the scalp and enter the dermis, the thickness of the needle wall 21 is configured as small as possible, so as to prevent the needle wall 21 of the micro-needle 20 being too thick and hence the time for the water-soluble polymer to dissolve being too long.

In addition, the height of the micro-needles 20 may be configured between 6.5 mm and 7.5 mm, e.g. 6.5 mm, 6.52 mm, 6.6 mm, 6.8 mm, 7 mm, 7.2 mm, 7.4 mm, or 7.5 mm, etc. The micro-needles 20 with height in this range would be easy to penetrate the scalp and enter the dermis, without further damaging the scalp of the patient.

In addition, the needle cavity 22 may also be configured to have a conical structure. The apex angle of the needle cavity 22 may accordingly be configured between 150 and 20°, e.g. 15°, 16°, 17.06°, 19°, 19.5°, or 20°, etc. The diameter of the bottom surface of the needle cavity 22 may accordingly be configured between 1.2 mm and 1.8 mm, e.g. 1.2 mm, 1.25 mm, 1.3 mm, 1.4 mm, 1.5 mm, or 1.8 mm, etc. The height of the needle cavity 22 may accordingly be configured between 3.5 mm and 5.5 mm, e.g. 3.5 mm, 3.52 mm, 3.6 mm, 3.8 mm, 4 mm, 4.2 mm, 4.4 mm, or 4.5 mm, etc.

Optionally, the fixing plate 30 is a fixing film, and the fixing film is configured to be attached to the micro-needles 20.

The fixing plate 30 is a fixing film, which has certain flexibility and elasticity, and is configured to be attached to the micro-needles 20. As a result, when applying the soluble needle 100 in this embodiment of the present disclosure in the hair transplantation surgery on the patient's scalp, pressing forces could be more conveniently and evenly applied to the scalp, improving the result of transplantation of the hair follicles. In addition, a fixing film is easier to be removed after the hair follicles accommodated in the cavity 22 become viable in the scalp.

Optionally, as shown in FIG. 1, a plurality of micro-needles 20 are configured to be fixed to the fixing plate 30 on the side of the needle cavities 22, and the fixing plate 30 is made of the same material as the micro-needles 20.

As a result, since the fixing plate 30 is made of the same material as the micro-needles 20, which means that the fixing plate 30 is also made of water-soluble polymers, one only needs to wipe away the dissolved fixing plate 30 with soft tissues or clothes when it gradually dissolves, rather than having to remove the fixing plate 30 fixedly connected to the micro-needles 20. The hair follicles are transferred between the fixing plate 30 and the needle cavities 22 of the micro-needles 20 in advance, after the micro-needles 20 of the soluble needle 100 penetrate the scalp and enter the dermis, the soluble needle 100 will entirely remain on the scalp of the patient. As the water-soluble polymers of the micro-needles 20 start to dissolve and to be absorbed by the human body gradually, the hair follicles become viable in the dermis and start to grow Since the fixing plate 30 is made of the same water-soluble polymers as the micro-needles 20, one only needs to wipe away the dissolved fixing plate 30, rather than having to remove it.

Optionally, the fixing plate 30 and the micro-needles 20 are detachably connected.

In the soluble needle 100 in this embodiment of present disclosure, the needle cavities 22 may be open cavities so that the hair follicles could be delivered into the needle cavities 22 in advance. For example, the needle cavity 22 may have an open end through which the hair follicles may be placed into the needle cavity 22. In one embodiment, as shown in FIG. 5, the micro-needle 20 has an open bottom connecting to the needle cavities 22. In another embodiment, a through hole may be created on the fixing plate 30, connecting to the needle cavity 22.

Alternatively, the needle cavities 22 may be closed cavities. In such embodiments the fixing plate 30 and the micro-needles 20 are detachably connected, so that when the hair follicles needed to be delivered, the fixing plate 30 may be detached from the micro-needles 20 to expose the needle cavities 22.

Here, the detachable connection could be configured as a bolting connection or a magnetic connection, wherein said bolting connection or magnetic connection includes two matching components installed on the fixing plate 30 and the micro-needle 20, respectively.

One embodiment of the bolting connection is illustrated herein. Specifically, the bolting connection comprises a bolt installed on the first member of connection and a nut installed on the second member of connection, wherein the bolt and the nut are matched to one and another.

The bolting connection comprise connecting units installed on the first member of connection and elastic bolt heads on ends of the connecting units. The nuts are surrounded by elastic fixing rings. The bolt heads are of sphere shapes. The bolt heads are of hollow structures, with blind holes extending from the connecting units to the bolt heads, so that the bolts on the first member of connection are allowed to elastically deform when compressed.

The bolts can be manufactured by integrated molding together with the first member of connection. The nuts present multiple nut holes, dividing the nuts into individual nutting units so that the nuts may elastically deform under external forces.

The diameter of the bolt heads is larger than that of the nuts. When the bolts bolt into the nuts, the nuts are pressed by the bolts and expand elastically, so as to allow the bolt heads pass through the nut holes. After the bolt heads pass through the nut holes, the nuts and the bolt heads all recover to original shapes. The bolt heads are held on the other side of the nut holes by the nuts so as to fix the first and second member of connection.

Chamfering is configured at the edges of the nuts so that when detaching the first member of connection from the second member of connection, the bolt heads are easily withdrawn from the nut holes under external forces.

Another embodiment of the bolting connection is illustrated herein. Specifically, the bolting connection comprises slot units and bolt units. The slot unit comprises a first slot, a second slot, and a hook between the first slot and the second slot, all of which are elastic.

The bolt unit comprises a first bolt, a second bolt, and a gib between the first bolt and the second bolt, all of which are elastic. When the bolt unit is connecting to the slot unit, the first bolt bolts into the first slot, the second bolt bolts into the second slot, and the hook connects with the gib. The elasticity of the first slot, the second slot, and the gib ensures that they are in close contact with the first bolt, the second bolt, and the hook, so as to achieve tight connection.

A third embodiment of the bolting connection may be illustrated herein. Specifically, the bolting connection comprises a male member and a female member, wherein the male member and female member are matching to one and another.

Here, the structures of the male member and the female member are not limited. Various embodiments of structures may exist, one of them being similar to the buckle applied on school bags.

Specifically, the female member comprises a cavity therein. The male member is of an E shape, i.e. the male member comprises a first arm, a third arm, and a second arm between the first arm and the third arm. The first arm and the third arm are elastic, and can bend towards the second arm under external forces. When the external forces are withdrawn, they will recover to their original positions. The second arm may be elastic or inelastic.

Correspondent to the male member, the front end of the female member is wider than the back end, wherein "front" takes reference to the forwarding position along the direction in which the male member enters the female member. The width of the front end of the female member is slightly smaller than the width of the male member, and the width of the back end of the female member is remarkably smaller than the width of the male member, so that, as the male member enters the female member, the first arm and the third arm are pushed towards the second arm when male member reaches the front end of the female member, and when the male member reaches the back end of the female member, the first arm and the third arm automatically recover to their original positions, extending out of the female member due to the cavity being open.

When connecting the male member and the female member, one could insert the male member into the female member, at which time the first arm and the third arm will extend out of the female member, and when detaching the male member and the female member, one only needs to squeeze the first arm and the third arm so that the male member could be withdrawn from the female member.

The magnetic connection may comprise electro-magnetic attracting units and attracted units. The electro-magnetic attracting units and the attracted units may be installed on the fixing plate 30 and the micro-needles 20 respectively. Here, the electro-magnetic attracting units may generate attracting force to the attracted units when powered, so as to bring the fixing plate 30 and the micro-needles 20 into connection.

As a result, when powered on, the electro-magnetic attracting units may generate attracting force to the attracted units, bringing the fixing plate 30 and the micro-needles 20 into connection; when powered off, the attracting force is terminated, and the fixing plate 30 will hence detach from the micro-needles 20.

Here, the working mechanism of the electro-magnetic attracting units is in the public domain, i.e. an energized conductor (e.g. a coil) generates a magnetic field to attract an object such as metal. The structure of the electro-magnetic attracting units may adopt what is in the public domain, e.g. electro-magnetic chunk or the like. The attracted units may be iron plates or iron blocks, or objects made of permanent magnets, etc.

Optionally, the micro-needles 20 and the fixing plate 30 may be manufactured by integrated molding, i.e. the micro-needles 20 and the fixing plate 30 are manufactured in the molding in one single process with the same materials. In addition, pinholes 24 may be created on the tips of the needles walls 21 of the micro-needles 20, communicating with the needle cavities 22. In embodiments described above, example of the micro-needles 20 and the fixing plate 30 being made of the same materials has been illustrated in detail, and therefore will not be repeated here.

As shown in FIG. 1, the fixing plate 30 may be square in shape. In such embodiment, the area of the square fixing plate 30 may be (55 mm~65 mm)×(55 mm~65 mm), for easy handling and application during surgery.

Another aspect of the embodiments of the present disclosure provides a method for manufacturing soluble needle 100 for hair transplantation, as shown in FIG. 6, comprising:

S101. dissolving the water-soluble polymers in water to prepare a molding solution;

S102. delivering the molding solution into a mold;

S103. letting the molding solution settle in the mold to shape; and

S104. separating and removing the mold to produce the soluble needle.

As shown in FIG. 6, the method of manufacturing soluble needle in this embodiment of the present disclosure includes firstly dissolving the water-soluble polymers in water to prepare an aqueous water-soluble polymer solution as a molding solution. Secondly, the prepared molding solution is delivered into a shaping mold, wherein the shaping mold is configured in advance to have female mold cavities matching the shape of the required micro-needles 20. As a result, molding solutions delivered into the mold will fill into the female mold cavities. Subsequently, the molding solution is allowed to settle in the mold to shape. Since the molding solution has the property of solidifying when settled statically, after a period of statically settling, the molding solution gradually solidifies to shape. Lastly, soluble needle 100 could be obtained by separating the mold from the shaped molding solution.

In the method in this embodiment of the present disclosure, no specific limitations are set to the mass fraction of the molding solution, provided that the molding solution is made from water-soluble polymers dissolved in water.

Optionally, the mass fraction of the molding solution is between 15 and 25 wt %, e.g. 15 wt %, 16 wt %, 18 wt %, 20 wt %, 22 wt %, 24 wt %, or 25 wt %, etc. Molding solution with mass fraction within this range is more convenient to handle and manufacture, produces a better shape, and is easier to dissolve and be absorbed by the human body.

Optionally, as shown in FIG. 7, letting the molding solution settle in the mold to shape includes:

S1031 letting the molding solution settle statically in the mold at an ambient temperature of 25° C. to 70° C., and with a settling time between 3 h and 24 h.

The ambient temperature is set between 25° C. and 70° C., e.g. 25° C., 26° C., 30° C., 40° C., 45° C., 47° C., 50° C., 60° C., 65° C., or 70° C., etc. Providing a more suitable ambient temperature to the molding solution to shape could accelerate the solidification process of the molding solution, and receive better shaping effect. In addition, the settling time is set between 3 h and 24 h, e.g. 3 h, 4 h, 8 h, 10 h, 13 h, 18 h, 22 h, 23 h, 24 h, etc. Too long or too short a settling time may cause negative effects to the applicability and reliability of the soluble needle produced by settling the molding solution to shape.

Optionally, as shown in FIG. 8, the method further includes S201 degassing treatment to the molding solution, before letting the molding solution settle in the mold to shape.

Performing degassing treatment to the molding solution before letting the molding solution settle to shape may effectively reduce the air bubbles possibly generated or trapped in the molding solution, and hence increase the yield in manufacturing the micro-needles 20.

Optionally, as shown in FIG. 9, delivering the molding solution into a mold includes:

S1021. injecting the molding solution into the mold, wherein the mold includes a plurality of mold cavities corresponding to the plurality of micro-needles 20, and the volume of molding solution injected into each mold cavity is less than the capacity of the mold cavity, so as to form a needle cavity 22 in the to-be-molded micro-needle structure in each mold cavity.

As shown in FIG. 9, when injecting the molding solution into the mold, in order to better form the desired structure of the needle cavity 22 inside the micro-needles 20, the volume of the molding solution injected into each mold cavity is less than the capacity of the mold cavity. Since the molding solution has a relatively high viscosity and a relatively large surface tension, it would adhere to the walls of the mold cavity when injected therein and hence form a structure of needle cavity 22 in the center of each mold cavity. By adjusting the volume of the molding solution injected into each mold cavity, one would be able to control and adjust the shape and size of the needle cavity 22 to some extent, so as to achieve the manufacture of the micro-needle 20 and the needle cavity 22 within one process only.

Optionally, as shown in FIG. 10, letting the molding solution settle in the mold to shape includes:

S1032 creating a through hole for each to-be-molded micro-needle structure in each mold cavity, so as to form a pinhole 24 at the tips of each to-be-molded micro-needle structure, with the pinhole communicating with the needle cavities 22.

When manufacturing the micro-needles 20 configured with pinholes 24 at the tip which are communicated with the needle cavities 22, letting the molding solution settle in the mold to shape may include creating through holes for each to-be-molded micro-needle structure, so as to form the required pinholes 24 at the tips of each to-be-molded micro-needle structure, and allow the pinholes 24 to communicate with the needle cavities 22.

In this process, the creation of pinholes 24 may be performed before or after the molding solution completely solidifies by settling statically, to which this embodiment of the present disclosure does not set limitations.

Where the above mentioned does not cover, the prior arts may apply.

Although the above terms concerning structures have been more frequently used, the possibility of using other terms should not be excluded. The use of the above terms is only for the purpose of more conveniently describing and explaining the essence of the present disclosure; considering them as any form of additional limitation is against the spirit of the present disclosure.

The above mentioned are merely specific embodiments of the present disclosure, to which the protection scope of the present disclosure should not be limited. Any modifications or substitutions, which those skilled in the art can obtain without any creative work based on the embodiments of the present disclosure, should all fall within the scope of the present disclosure. Therefore, the scope of protection of the present disclosure should be determined by the scope of the claims.

INDUSTRIAL APPLICABILITY

The present disclosure provides soluble needles for hair transplantation and a method of manufacturing the same. By transferring the hair follicles to be transplanted into the soluble needles in advance, one only needs to control the soluble needles to penetrate the scalp and enter the dermis of the scalp during the hair transplantation surgery, which would then enable the hair follicles to survive and start to grow in a relatively stable and suitable environment. This effectively shortens the time of the hair transplantation surgery, reduces the pain of the patients, and increases the viability rate of transplanted hair follicles and hence the success rate of hair transplantation surgery

The invention claimed is:

1. A method of hair transplantation comprising:
providing a soluble needle device that includes a fixing plate and a plurality of micro-needles arranged on the fixing plate, wherein each micro-needle has a tapered body that is made of a water-soluble polymer and has a needle cavity containing a hair follicle; and
penetrating a scalp of a subject with the soluble needle device to implant the plurality of micro-needles containing the hair follicle into dermis of the scalp.

2. The method of claim 1, comprising placing the hair follicle into the cavity of each of the plurality of micro-needles before implanting into the dermis of the scalp.

3. The method of claim 2, comprising:
providing each of the plurality of micro-needles to have an open end opposite of a tip; and
covering each open end of the plurality of micro-needles with the fixing plate to contain the hair follicle in the needle cavity.

4. The method of claim 1, comprising retaining the implanted plurality of micro-needles containing the hair follicle in the dermis of the scalp so that the plurality of micro-needles dissolve.

5. The method of claim 1, comprising dissolving the plurality of micro-needles in the dermis of the scalp so that each hair follicle is exposed to blood of the subject.

6. The method of claim 1, comprising growing the hair follicle in the dermis of the scalp.

7. The method of claim 6, wherein the hair follicle is grown without intervention.

8. The method of claim 1, wherein the fixing plate is made of a water-soluble polymer, the method comprising at least partially dissolving the fixing plate.

9. The method of claim 8, comprising removing the at least partially dissolved fixing plate from the scalp.

10. The method of claim 1, comprising removing the fixing plate when detachable from the plurality of micro-needles that are implanted in the dermis of the scalp.

11. The method of claim 1, wherein the cavity is conical.

12. The method of claim 1, wherein a connecting layer connects each of the plurality of micro-needles together, wherein the connecting layer is made of a water-soluble polymer, the method comprising removing the connecting layer from the scalp after at least partially degrading.

13. The method of claim 1, wherein the plurality of micro-needles are implanted at a density of 20 to 40 micro-needles per square centimeter.

14. The method of claim 1, wherein a tip of each of the plurality of micro-needles includes a pin hole that allows body fluid to enter into the needle cavity containing the hair follicle.

15. The method of claim 1, wherein the fixing plate is a flexible fixing film.

16. The method of claim 1, wherein each needle cavity is a closed cavity containing the hair follicle.

17. The method of claim 1, wherein the soluble needle device comprises:
   each needle cavity has a closed base end and is configured for accommodating a hair follicle;
   each micro-needle has a conical structure; and
   each needle cavity is conical.

18. The method of claim 1, wherein the soluble needle device comprises:
   each micro-needle has a conical structure;
   each needle cavity is conical;
   an apex angle of each micro-needle is between 15° and 20°; and
   a diameter of a bottom surface of each micro-needle is between 2.2 mm and 2.8 mm.

19. The method of claim 1, wherein the soluble needle device comprises:
   each micro-needle has a conical structure;
   each needle cavity is conical; and
   each micro-needle is detachably connected to the fixing plate.

20. The method of claim 1, wherein the soluble needle device comprises the plurality of micro-needles being connected to each other.

* * * * *

UNITED STATES PATENT AND TRADEMARK OFFICE
CERTIFICATE OF CORRECTION

| | |
|---|---|
| PATENT NO. | : 12,075,993 B2 |
| APPLICATION NO. | : 18/107402 |
| DATED | : September 3, 2024 |
| INVENTOR(S) | : Sulaiman Abdulmohsin Almalaq et al. |

It is certified that error appears in the above-identified patent and that said Letters Patent is hereby corrected as shown below:

On the Title Page

Column 1, Item (30), insert:
--Foreign Application Priority Data:
Aug. 24, 2017 (CN) ..........................201710733590.2--

Signed and Sealed this
First Day of April, 2025

Coke Morgan Stewart
*Acting Director of the United States Patent and Trademark Office*